United States Patent [19]

Lerman et al.

[11] Patent Number: 4,954,648

[45] Date of Patent: Sep. 4, 1990

[54] METHOD FOR THE BROMINATION OF AROMATIC COMPOUND

[75] Inventors: Ori Lerman, Ramat-Gan; Shlomo Rozen, Tel-Aviv, both of Israel

[73] Assignees: Ramot University Authority of Applied Research and Industrial Development Ltd.; ICL Industries Ltd., both of Israel

[21] Appl. No.: 350,394

[22] Filed: May 11, 1989

[30] Foreign Application Priority Data

May 12, 1988 [IL] Israel ......................................... 86353

[51] Int. Cl.$^5$ ..................... C07C 121/52; C07C 69/72
[52] U.S. Cl. ....................................... 558/425; 560/83; 560/103; 560/104; 568/937; 570/127; 570/182; 570/185; 570/261
[58] Field of Search ................ 558/425; 560/103, 104, 560/83; 568/937; 570/182, 185, 261, 127

[56] References Cited

U.S. PATENT DOCUMENTS 4,739,057  4/1988  Leone-Bay et al. ................ 570/182

*Primary Examiner*—Mary C. Lee
*Assistant Examiner*—J. Richter
*Attorney, Agent, or Firm*—Brumbaugh, Graves, Donohue & Raymond

[57] ABSTRACT

A method for the bromination of aromatic compounds, including substituted deactivated aromatic compounds, at mild temperature conditions is disclosed. The method comprises reacting an aromatic compound with a bromination agent consisting of bromine-trifluoride and bromine at a temperature ranging between $-10°$ C. and $30°$ C. The bromination reaction takes place instantaneously and the brominated aromatic compound is separated from the original reactant by known organic chemistry techniques.

10 Claims, No Drawings

METHOD FOR THE BROMINATION OF AROMATIC COMPOUND

The present invention relates in general to a method for the bromination of aromatic compounds and to brominated compounds obtained thereby. In particular, the invention relates to a process for the bromination of substituted, deactivated benzenoid aromatic compounds.

BACKGROUND OF THE INVENTION

Brominated aromatic compounds possess a wide spectrum of industrial applications, such as in the pharmaceutical industry, as fire retardants, as herbicides, biocides and as various intermediates in organic synthesis.

Most aromatic bromination processes in current use are carried out in the presence of various Lewis acids serving as catalyst. Those known processes suffer from many disadvantages, such as the requirement of large amounts of catalyst, the requirement for anhydrous conditions and the substantial amounts of sewage discharged, which often rise serious disposal problems. Furthermore, bromination of aromatic compounds, in particular non-activated aromatic compounds, is a time consuming process, and the yields obtained by the known processes are relatively low.

Another known bromination route consists of the diazotation of the corresponding anilines, followed by thermal decomposition in the presence of bromide ion. Such route suffers from the disadvantages that it requires a suitable aniline derivative which is not always commercially available and that the required reaction periods are generally long.

A recently published research by S. Rozen and M. Brand in J. Chem. Soc. Chen. Comm. (1987) pages 752 and 753 discloses a process for the bromination of aromatic compounds utilizing bromine fluoride as the brominating agent. The bromine fluoride is prepared in situ by bubbling fluorine through a solution of bromine suspended in an organic solvent such as trichlorofluoromethane, at a low temperature ranging between $-45°$ C. to $-78°$ C. The major disadvantages of the above process rises from the extensive cooling and the large quantities of solvent required for preparing the brominating reagent. The large quantities of solvent are required, since concentrated solutions of bromine fluoride tend to decompose. As a result, only small amounts of the aromatic compounds can be brominated, or alternatively exceptionally sizable reactors are required.

BRIEF DESCRIPTION OF THE INVENTION

It is thus the object of the present invention to overcome the disadvantages of the known methods for the bromination of aromatic compounds and to provide for a method which can be carried out at non-extreme temperature conditions, a method which neither requires the use of catalysts, nor the use of solvents when the aromatic compound to be brominated is at a liquid state at the temperature of the reaction, and which provides fair yields at a relatively short reaction periods.

Thus, in accordance with the present invention there is provided a method for the bromination of an aromatic compound comprising reacting the aromatic compound with a bromination agent comprising bromine-trifluoride and bromine at a temperature above about minus ten degrees centigrade and separating the obtained brominated aromatic compound from the original reactants by known organic techniques.

The bromination agent of the invention can be a preprepared mixture of bromine and bromine-trifluoride. Alternatively, the bromine is first added to the aromatic compound and the bromine-trifluoride is subsequently added to the reaction mixture.

The bromination reaction, according to the invention, takes place instantaneously. However, since the reaction is exothermic, it is preferable to add the mixture of the bromination agent to the aromatic compound at a rate allowing to control the temperature of the reaction. Thus, when a mixture of bromine and bromine-trifluoride is used, the mixture is added to the aromatic compound dropwise, whereas when the bromine is first added to the aromatic compound, the bromine-trifluoride is added dropwise. Alternatively, the bromination mixture can be swept by a stream of nitrogen into the aromatic compound.

The prefered temperature of the reaction ranges between $-10$ C. and $30°$ C.

Preferably, the bromination agent consists of equimolar amounts of bromine-trifluoride and bromine, or the bromine is in slight excess to the bromine-trifluoride. It is also preferable that the aromatic compound to be brominated is in molar excess to the molar content of bromine in the bromination agent.

In order to effect a decrease in the melting point of the compound to be brominated, minute amount of solvent can be added to the aromatic compound prior to the addition of the bromination mixture. When the aromatic compound is a solid material at the temperature of the reaction, the aromatic compound should be dissolved or suspended prior to its reaction with the bromination agent. The solvent can be any inert solvent. Preferably perhalogenated solvents such as freon 11 or freon 113 are suitable.

The bromination agent of the invention reacts with deactivated benzenoid rings to provide the expected bromo substituents without affecting any functional groups. The selectivity of the reaction is dependent on the substrate to be brominated. Thus, deactivated aromatic compounds, such as nitrobenzene, benzotrifluoride or methyl benzoate are brominated at the meta position whereas benzonitril yields meta and ortho bromobenzonitrils. Non-activated aromatic compounds such as chlorobenzene and bromobenzene yield relatively small amounts of para and ortho derivatives with considerable amounts of tar and polybrominated compounds.

DETAILED DESCRIPTION OF THE INVENTION

The advantages of the bromination process of the invention will be better demonstrated throughout the following representative non-limiting examples. The reaction products obtained as described in the following examples were analysed by gas-chromatographic analysis. Analysis were conducted using 25 m long capillary columns with internal standards. NMR spectra, of all the products obtained, are in excellent agreement with the corresponding published NMR spectra.

EXAMPLE 1—BROMINATION OF NITROBENZENE AT 0°–10° C.

A vigorously stirred mixture consisting of 0.1 moles (5 ml) bromine-trifluoride and 0.12 moles (6.5 ml) of bromine was added into a brine cooled three-necked flask equipped with a magnetic stirrer and a condenser containing ca. 0.6–0.7 moles of nitrobenzene. The addition was carried out dropwise with vigorous stirring while the temperature was kept between zero and ten degrees centigrate. After the addition was completed the crude reaction mixture was poured into a stirred icy 5% sodium sulfite solution. The organic layer was separated, and the aqueous solution was extracted twice with two portions of 100 ml dichloromethane. The combined organic layer was washed with 5% sodium bicarbonate solution and successively with water. The organic phase was dried over anhydrous magnesium sulfate and the solvent evaporated. The crude reaction mixture was quantitatively analyzed by gas-chromatography internal standard program. The meta-bromonitrobenzene obtained was separated from the starting material by reduced pressure distillation. The yield of meta-bromonitrobenzene obtained, expressed in percentage of pure meta-bromonitrobenzene obtained based on reacted nitrobenzene, is 81%.

EXAMPLE 2—BROMINATION OF NITROBENZENE AT 10°–20° C.

Bromination of nitrobenzene at a temperature ranging between ten and twenty degrees centigrade was carried out according to a procedure similar to the procedure described in example 1. The yield of pure metabromonitrobenzene obtained is 52%.

EXAMPLES 3 AND 4—BROMINATION OF NITROBENZENE BELOW 0° C.

Brominations of nitrobenzene at temperatures below zero degrees centigrade were carried out according to a procedure similar to the procedure described in example 1. The reaction was carried out in the presence of freon 11 in order to effect a decrease in the melting point of nitrobenzene. 5 ml of freon 11 was added to the flask containing the nitrobenzene prior to the addition of the bromination mixture. The yield of meta-bromonitrobenzene obtained at the temperature ranging between zero and minus five degrees centigrade was 72% and the yield between zero and minus ten degrees centigrade was 60%.

EXAMPLES 5 TO 14

Bromination of the substituted, deactivated benzenoid aromatic compounds benzonitrile, benzotrifluoride, methylbenzoate, diethyl phthalate and diethyl isophthalate and the non-activated compound chlorobenzene were carried out according to procedures, similar to the procedure described in the above examples, with the following results:

| Example No. | Starting Material | Product(s) | Yield | Temperature Range |
|---|---|---|---|---|
| 5 | $C_6H_5CN$ | m-Br—$C_6H_4CN$ | 44% | −10°–0° |
|   |   | o-Br—$C_6H_4CN$ | 12.5% |   |
| 6 | $C_6H_5CN$ | m-Br—$C_6H_4CN$ | 43% | 0°–10° |
|   |   | o-Br—$C_6H_4CN$ | 12.5% |   |
| 7 | $C_6H_5CF_3$ | m-Br—$C_6H_4CF_3$ | 62% | −10°–0° |
| 8 | $C_6H_5CF_3$ | m-Br—$C_6H_4CF_3$ | 65% | 0°–10° |
| 9 | $C_6H_5COOCH_3$ | m-Br—$C_6H_4COOCH_3$ | 49% | 5°–10° |
| 10 | $C_6H_5COOCH_3$ | m-Br—$C_6H_4COOCH_3$ | 60% | −10°–0° |
| 11 | $C_6H_5COOCH_3$ | m-Br—$C_6H_4COOCH_3$ | 64% | −5°–5° |
| 12 | $C_6H_5Cl$ | p-Br—$C_6H_4Cl$ | 25% | −15°– −10° |
|   |   | m-Br—$C_6H_4Cl$ | 5% |   |
| 13 | 1,3-di($COOC_2H_5$) $C_6H_4$ | 1,3-di($COOC_2H_5$) 5-Br—$C_6H_3$ | 55% | 5°–15° |
| 14 | 1,2-di($COOC_2H_5$) $C_6H_4$ | 1,2-di($COOC_2H_5$) 3-Br—$C_6H_3$ | 32% | 5°–15° |
|   |   | 1,2-di($COOC_2H_5$) 4-Br—$C_6H_3$ | 34% |   |

EXAMPLE 15

A vigorously stirred mixture consisting of 2.5 ml (0.05 mole) of bromine trifluoride and 3.2 ml (0.056 mole) of bromine was added into an ice-water cooled three necked flask equipped with a magnetic stirrer and a condenser, containing a suspension of 36 gr (0.2 mole) 3-nitroacetophenone in 80 ml of freon 113. The addition was carried out dropwise with vigorous stirring while the temperature was kept under 20° C.

After the addition was completed the crude reaction mixture was poured into a stirred icy 5% sodium sulfite solution. The organic layer was separated and the aqueous solution was extracted twice with 100 ml dichloromethane. The combined organic layer was washed with 5% sodium bicarbonate solution and successively with water. The organic phase was dried over anhydrous magnesium sulphate and the solvent evaporated. The residue was distilled under reduced pressure in order to get rid of unreacted substrate. The residue was recrystalized from toluene. 7.3 gr of 3-bromo-5-nitroacetophenone were obtained, 85% yield based on reacted substrate.

EXAMPLES 16 TO 20

Bromination of the following substituted deactivated solid benzenoid aromatic compounds was carried out according to procedures similar to the procedure described in example 15 with the following results:

| Example No. | Starting Material | Product(s) | Solvent | Yield | Temperature Range |
|---|---|---|---|---|---|
| 16 | 1-($COCH_3$) 3-($NO_2$)—$C_6H_4$ | 1-($COCH_3$)3-Br 5-($NO_2$)—$C_6H_3$ | $CHCl_3$ | 27% | 15–20° |
| 17 | 1-($COCH_3$) 4-($NO_2$)—$C_6H_4$ | 1-($COCH_3$)2-Br 4-($NO_2$)—$C_6H_3$ | Freon 113 | 89% | 15–25° |
| 18 | 1-($CH_3$) 4-($NO_2$)—$C_6H_4$ | 1-($CH_3$)2-Br 4-($NO_2$)—$C_6H_3$ | Freon 113 | 41% | 15–20° |

-continued

| Example No. | Starting Material | Product(s) | Solvent | Yield | Temperature Range |
|---|---|---|---|---|---|
| 19 | 1,4-di(COOCH$_3$)C$_6$H$_4$ | 1,4-di(COOCH$_3$)2-Br—C$_6$H$_3$ | Freon 113 | 53% | 15–10° |
| 20 | 1,3-di(NO$_2$)C$_6$H$_4$ | 1,3-di(NO$_2$)5-Br—C$_6$H$_3$ | Freon 113 | 62% | 15–20° |

EXAMPLE 21—BROMINATION OF BENZOTRIFLUORIDE 60 gr of benzotrifluoride and 8 ml of bromine were placed in a three necked flask equipped with a thermometer and a mechanical stirrer. The mixture was cooled to 5°–10° C. and 14 gr (5 ml) of brominetrifluoride was introduced dropwise into the mixture under vigorous stirring while the temperature was kept under 15° C. (ice bath). When the addition was completed 50 ml of 10% sodium sulfite solution was added and the mixture was stirred vigorously. The organic layer was separated, and the aqueous layer was extracted with two portions of 50 ml of dichloromethane. The combined organic layer was washed with 25 ml of sodium bicarbonate solution and with two portions of 50 ml of water, and dried over anhydrous magnesium sulfate. The solvent was stripped off by distillation and then the excess of the substrate was distilled at atmospheric pressure. 28 ml of unreacted benzotrifluoride was obtained. The residue was distilled at 20 mm Hg and 31 gr of 3-bromobenzotrifluoride was obtained, 63% yield based on reacted benzotrifluoride.

EXAMPLE 22—BROMINATION OF BENZOTRIFLUORIDE WITH A BROMINATION MIXTURE SWEPT BY A NITROGEN STREAM 24 gr of bromine and 14 gr of brominetrifluoride were placed in a 50 ml three necked flask. The mixture was stirred vigorously and swept by the aid of a stream of dry nitrogen into a 250 ml three necked flask equipped with a mechanical stirrer, thermometer and double faced condensor, containing 60 gr of benzotrifluoride. Both mixtures were stirred vigorously and icy water was circulated through the condensor, until all the mixture was swept over to the second flask. When no mixture was left in the first flask the reaction was stopped and treated as described in example 21. 25 gr of benzotrifluoride was recovered under distillation and 33 gr of 3-bromobenzotrifluoride was obtained, 61% yield based on reacted benzotrifluoride.

I claim:

1. A method for the bromination of an aromatic compound comprising reacting said aromatic compound with a bromination agent comprising bromine-trifluoride and bromine at a temperature of above about minus ten degrees centigrade, and separating the obtained brominated aromatic compound from the original reactants by known organic chemistry techniques.

2. A method for the bromination of an aromatic compound according to claim 1 wherein the aromatic compound is a deactivated benzenoid compound.

3. A method for the bromination of an aromatic compound according to claim 1 wherein the temperature of the reaction ranges between −10° C. and 30° C.

4. A method for the bromination of an aromatic compound according to claim 1 wherein the melting point of said aromatic compound is above the temperature of the reaction, comprising a further step of adding a solvent to the aromatic compound prior to the reaction with the bromination agent.

5. A method for the bromination of an aromatic compound according to claim 4 wherein minute amount of solvent is added to the aromatic compound in order to effect a decrease in the melting point of the compound to be reacted.

6. A method for the bromination of an aromatic compound according to claim 4 wherein substantial amount of solvent is added to the aromatic material to dissolve or suspend said aromatic material.

7. A method for the bromination of an aromatic compound according to claim 4 wherein the solvent is an inert perhalogenated solvent.

8. A method for the bromination of an aromatic compound according to claim 1 wherein the aromatic compound to be brominated is in molar excess to the bromine content at the bromination agent.

9. A method for the bromination of an aromatic compound according to claim 1 wherein the brominated agent is added to the aromatic compound dropwise.

10. A method for the bromination of an aromatic compound according to claim 1 wherein the brominated agent is swept into the aromatic compound by a stream of inert gas.

* * * * *